US012616465B2

(12) United States Patent
 Zhang

(10) Patent No.: US 12,616,465 B2
(45) Date of Patent: May 5, 2026

(54) SURGICAL STAPLING APPARATUS WITH LOCKOUT ASSEMBLY

(71) Applicant: Covidien LP, Mansfield, MA (US)

(72) Inventor: Guowei Zhang, Shanghai (CN)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/025,778

(22) PCT Filed: Sep. 17, 2020

(86) PCT No.: PCT/CN2020/115719
 § 371 (c)(1),
 (2) Date: Mar. 10, 2023

(87) PCT Pub. No.: WO2022/056753
 PCT Pub. Date: Mar. 24, 2022

(65) Prior Publication Data
 US 2023/0338021 A1     Oct. 26, 2023

(51) Int. Cl.
 *A61B 17/072* (2006.01)
 *A61B 17/00* (2006.01)
 *A61B 17/28* (2006.01)
 *A61B 90/00* (2016.01)

(52) U.S. Cl.
 CPC .... *A61B 17/072* (2013.01); *A61B 2017/0023* (2013.01); *A61B 2017/07257* (2013.01); *A61B 2017/07271* (2013.01); *A61B 17/2833* (2013.01); *A61B 2090/0808* (2016.02)

(58) Field of Classification Search
 CPC ............ A61B 17/072; A61B 17/07207; A61B 17/2833; A61B 2017/07257; A61B 2017/07271; A61B 2017/0023; A61B 2090/0808; A61B 2090/0811

USPC .......................................... 227/175.3, 175.2
See application file for complete search history.

(56) References Cited

U.S. PATENT DOCUMENTS

| | | | |
|---|---|---|---|
| 4,508,253 A | | 4/1985 | Green |
| 5,673,842 A | * | 10/1997 | Bittner ............. A61B 17/07207 |
| | | | 227/180.1 |
| 5,878,938 A | | 3/1999 | Bittner et al. |
| 5,893,506 A | * | 4/1999 | Powell ............. A61B 17/07207 |
| | | | 227/176.1 |

(Continued)

FOREIGN PATENT DOCUMENTS

| | | |
|---|---|---|
| CN | 114191017 A | 3/2022 |
| CN | 217138146 U | 8/2022 |

OTHER PUBLICATIONS

International Search Report for Application No. PCT/CN2020/115719 dated Jun. 17, 2021.

(Continued)

*Primary Examiner* — Linda J. Hodge

(57) ABSTRACT

A surgical stapling apparatus includes an anvil half-section, a cartridge receiving half-section, a firing assembly including a push plate, and a lockout assembly. The cartridge receiving half-section defines an elongated channel member configured to receive a single use loading unit (SULU). The lockout assembly is supported in the elongated channel member and includes a lockout assembly that is selectively engageable with the push plate to prevent movement of the push plate relative to the lockout assembly when the anvil half-section and the cartridge receiving half-section are not secured together.

20 Claims, 8 Drawing Sheets

(56)             References Cited

U.S. PATENT DOCUMENTS

| | | | |
|---|---|---|---|
| 5,902,312 | A | 5/1999 | Frater et al. |
| 6,131,789 | A | 10/2000 | Schulze et al. |
| 7,334,717 | B2 * | 2/2008 | Rethy ................. A61B 17/105 |
| | | | 227/175.3 |
| 7,631,794 | B2 | 12/2009 | Rethy et al. |
| 10,512,461 | B2 | 12/2019 | Gupta et al. |
| 10,765,424 | B2 | 9/2020 | Baxter, III et al. |
| 2010/0065606 | A1 | 3/2010 | Stopek |
| 2012/0312861 | A1 | 12/2012 | Gurumurthy et al. |
| 2013/0264370 | A1 * | 10/2013 | Chen ................ A61B 17/07207 |
| | | | 227/175.2 |
| 2015/0265275 | A1 * | 9/2015 | Chen ................ A61B 17/07207 |
| | | | 227/175.3 |
| 2019/0159777 | A1 | 5/2019 | Ehrenfels et al. |
| 2019/0239882 | A1 * | 8/2019 | McLain .............. A61B 17/1114 |
| 2021/0038223 | A1 * | 2/2021 | Schings ............. A61B 17/0644 |
| 2022/0061836 | A1 * | 3/2022 | Parihar ................ A61B 17/072 |

OTHER PUBLICATIONS

Written Opinion for Application No. PCT/CN2020/115719 dated Jun. 17, 2021.
Office Action for Chinese Patent Application No. 202111083540.7 mailed Mar. 28, 2025, 20 pages.

* cited by examiner

26a

8

8

26a

26a

SURGICAL STAPLING APPARATUS WITH LOCKOUT ASSEMBLY

TECHNICAL FIELD

This disclosure relates to surgical stapling apparatus and, more particularly, to surgical stapling apparatus having reusable and disposable components.

BACKGROUND

Surgical stapling apparatus that clamp tissue between opposing jaw structures and fasten the clamped tissue with surgical staples are well known in the art. In such apparatus, a knife is often provided to cut the tissue joined by the staples.

Surgical stapling apparatus often include two elongated beam members which are used to capture or clamp tissue therebetween. Typically, one of the beam members carries a disposable cartridge assembly which houses a plurality of staples arranged in at least two lateral rows, while the other beam member includes an anvil that defines a surface for forming the staple legs as the staples are driven from the cartridge assembly. Where two-part fasteners are used, the beam member which includes the anvil carries a mating part of the two-part fastener, e.g., the receiver. Generally, the staple formation process is affected by the interaction between one or more longitudinally moving camming members and a series of individual staple pushers. As the camming members travel longitudinally through the cartridge carrying beam member, the individual pusher members are biased upwardly into a backspan of the staples supported within the cartridge assembly to sequentially eject the staples from the cartridge. A knife may be provided to travel with the camming members between the staple rows to cut the tissue between the rows of formed staples. An example of such an instrument is disclosed in U.S. Pat. No. 7,631,794, which is incorporated herein in its entirety by reference.

SUMMARY

According to one aspect of this disclosure, a surgical stapling apparatus includes an anvil half-section, a cartridge receiving half-section, a firing assembly including a push plate, and a lockout assembly. The cartridge receiving half-section defines an elongated channel member configured to receive a single use loading unit (SULU). The lockout assembly is supported in the elongated channel member and includes a lockout assembly that is selectively engageable with the push plate to prevent movement of the push plate relative to the lockout assembly when the anvil half-section and the cartridge receiving half-section are not secured together.

In aspects of this disclosure, the lockout assembly may include a stopper and the push plate may defines a lockout recess that is configured to receive the stopper of the lockout assembly therein.

In various aspects of this disclosure, the lockout assembly may include a lockout and a spring unit secured to the lockout. The spring unit may be positioned in engagement with the push plate. The spring unit may include a leaf spring that contacts the push plate and biases the push plate in a locked position. The leaf spring may be positioned to move between a first position and a second position, wherein in the first position, the lockout maintains the push plate in the locked position and prevents the push plate from moving distally beyond the lockout, and wherein in the second position, the push plate is positioned to advance through the lockout. The lockout may define a push plate passage through a support wall of the lockout. The support wall of the lockout may be supported between legs of the lockout. The legs may include shoulders that are receivable by support apertures defined in the elongated channel member to fixedly secure the lockout to the elongated channel member. The legs may include feet that support the lockout. The feet may include nubs that extend laterally from the feet to secure the spring unit to the lockout. The SULU may include a proximal flange positioned to engage the push plate. The proximal flange may be vertically movable relative to elongated channel member to move the leaf spring from the first position to the second position.

According to another aspect of this disclosure, a surgical stapling apparatus includes an anvil half-section, a cartridge receiving half-section defining an elongated channel member, a push plate, and a lockout assembly. The elongated channel member is configured to receive a single use loading unit (SULU). The lockout assembly is selectively engageable with the push plate to lock the push plate at an acute angle relative to the elongated channel member when the anvil half-section and the cartridge receiving half-section are not secured together.

In aspects of this disclosure, the lockout assembly may include a stopper and the push plate may define a lockout recess that maintains the stopper therein when the push plate is disposed at the acute angle relative to the elongated channel member.

In various aspects of this disclosure, the lockout assembly may include a lockout and a spring unit secured to the lockout. The spring unit may be positioned in engagement with the push plate to maintain the push plate at the acute angle. The spring unit may include a leaf spring that contacts the push plate. The leaf spring may be positioned to move between a first position and a second position, wherein in the first position, the lockout prevents the push plate from moving distally beyond the lockout, and wherein in the second position, the push plate is positioned to advance through the lockout. The lockout may define a push plate passage through a support wall of the lockout to enable the push plate to advance through the lockout when the leaf spring is disposed in the second position. The support wall of the lockout may be supported between legs of the lockout and may extend above the leaf spring. The legs may include shoulders received in support apertures defined in the elongated channel member to prevent the lockout from moving relative to the elongated channel member. The legs may include feet that support the lockout. The feet may include nubs that extend from the feet to secure the spring unit to the lockout. The SULU may include a proximal flange positioned in contact with a top surface of the push plate. The proximal flange may be movable relative to elongated channel member to move the leaf spring from the first position to the second position.

The details of one or more aspects of this disclosure are set forth in the accompanying drawings and the description below. Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with the detailed description of the embodiments given below, serve to explain the principles of the disclosure.

Figure 1:
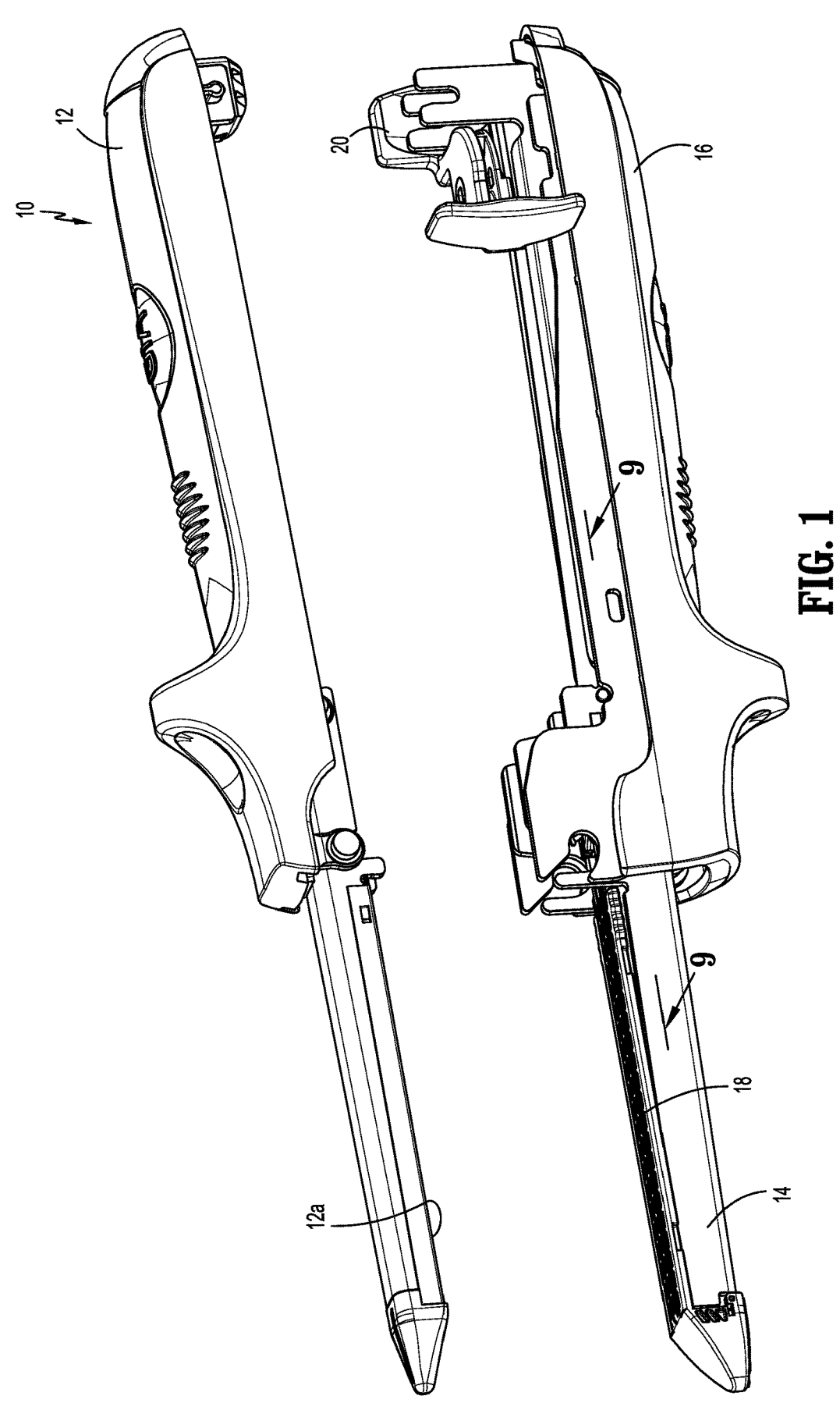
Figure 2:
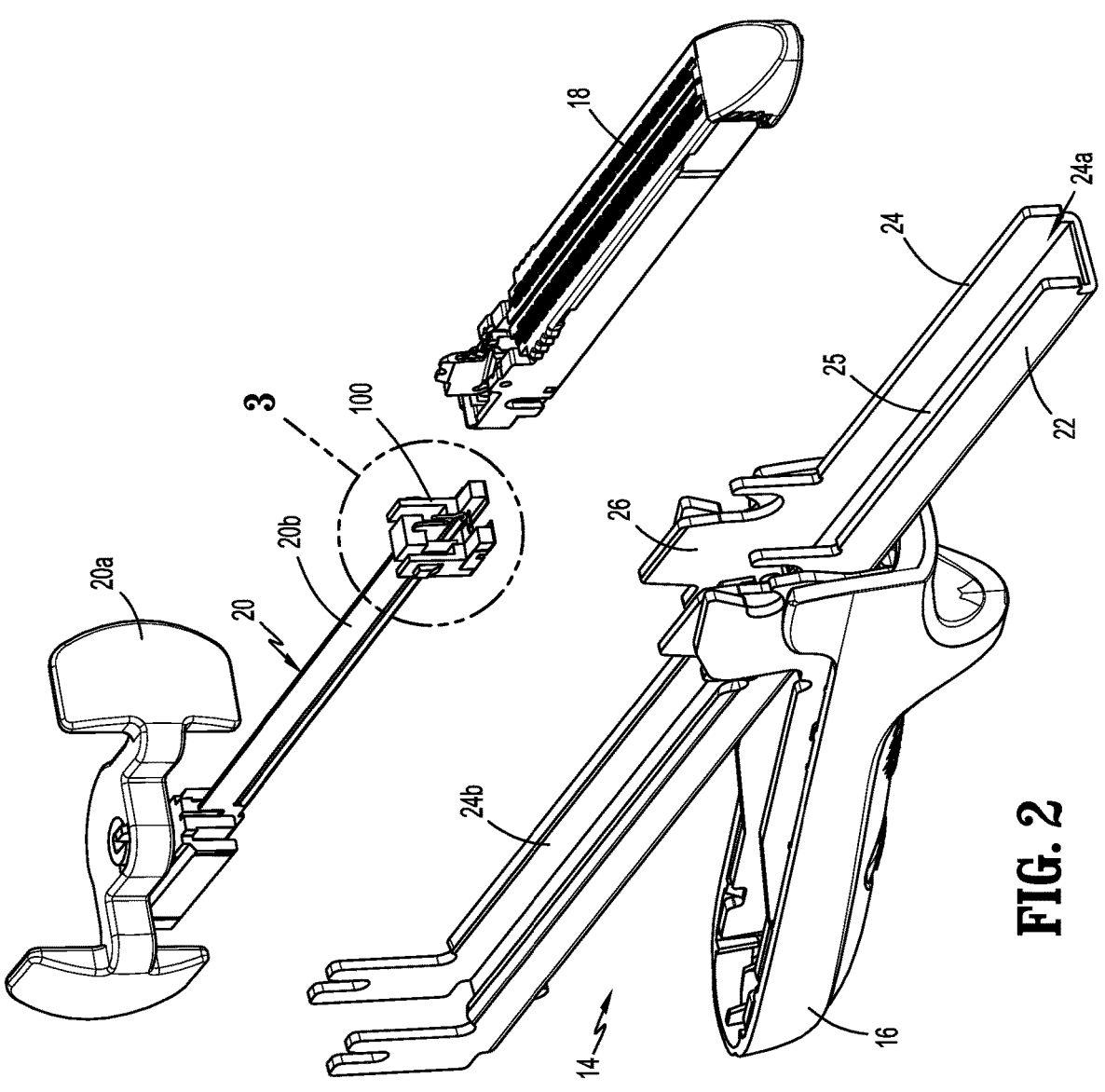
Figures 3, 4:
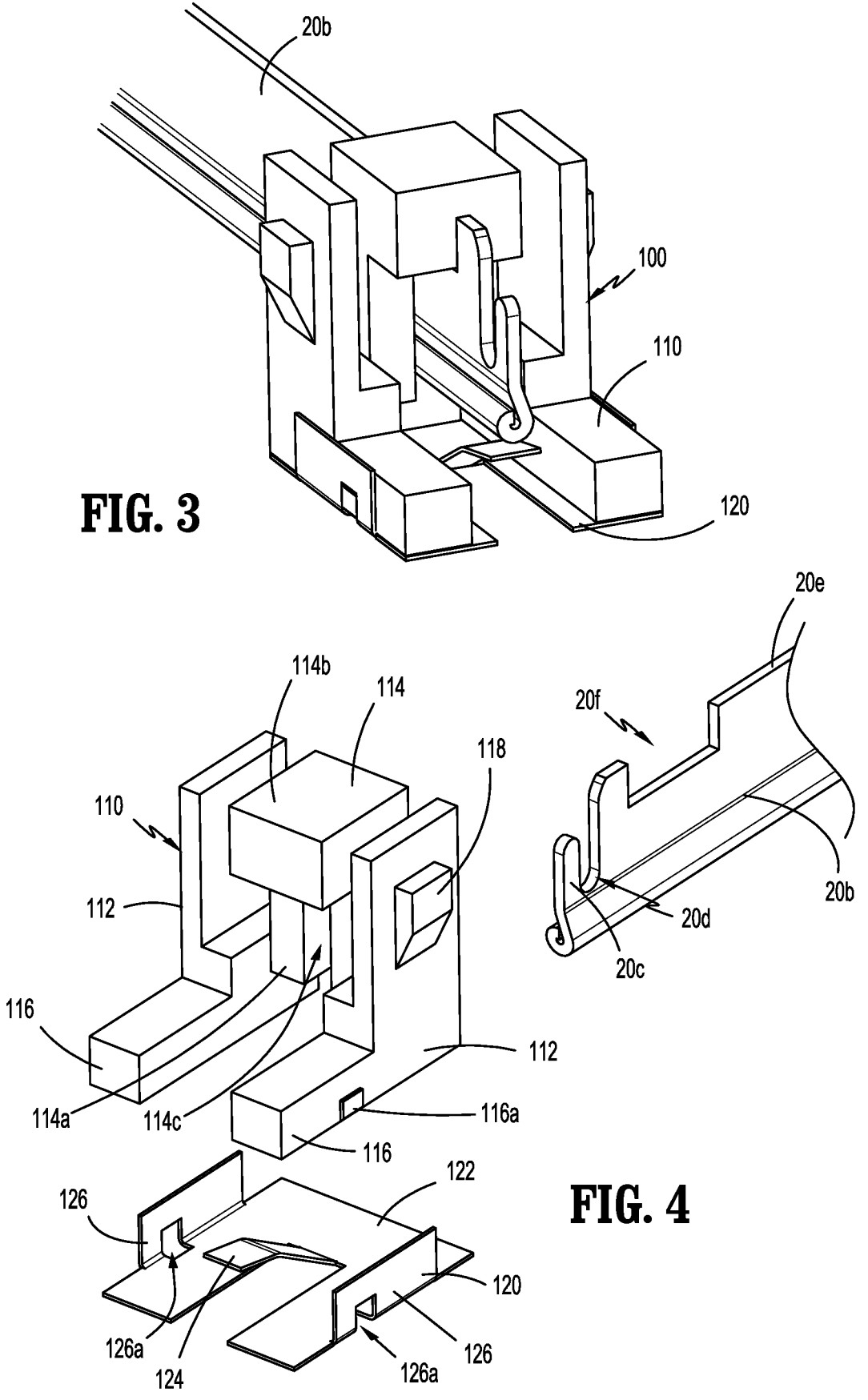
Figure 5:
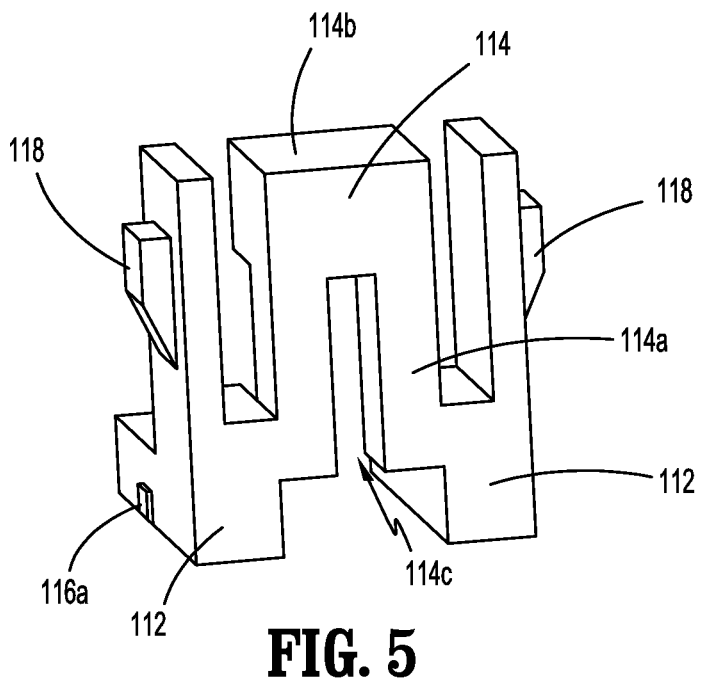
Figure 6:
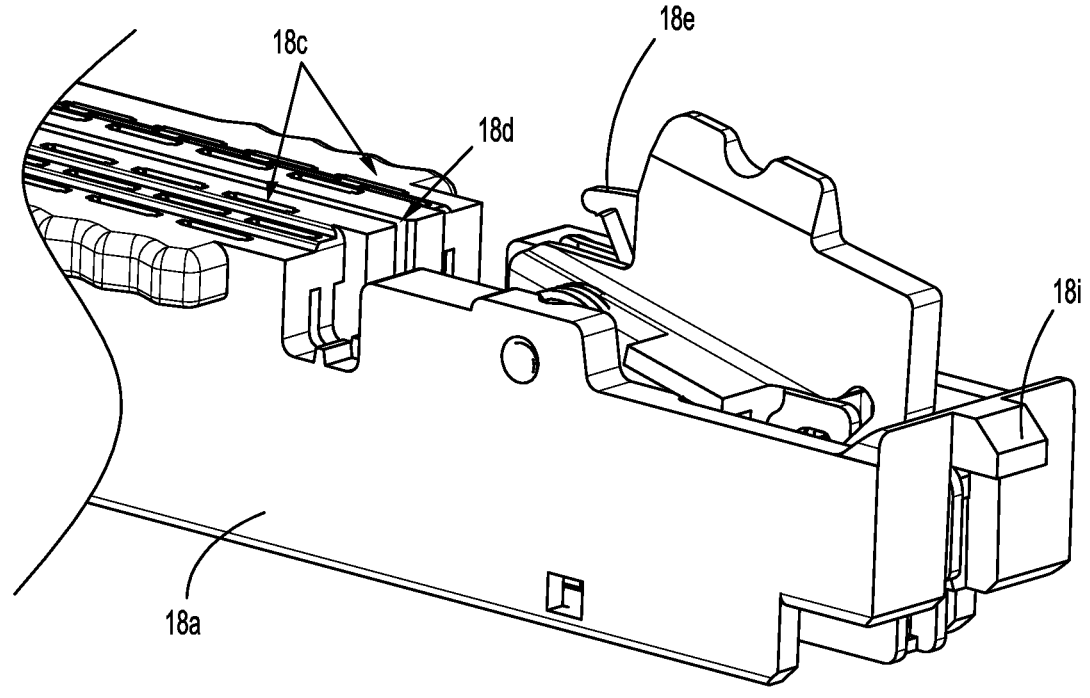
Figures 7, 8:
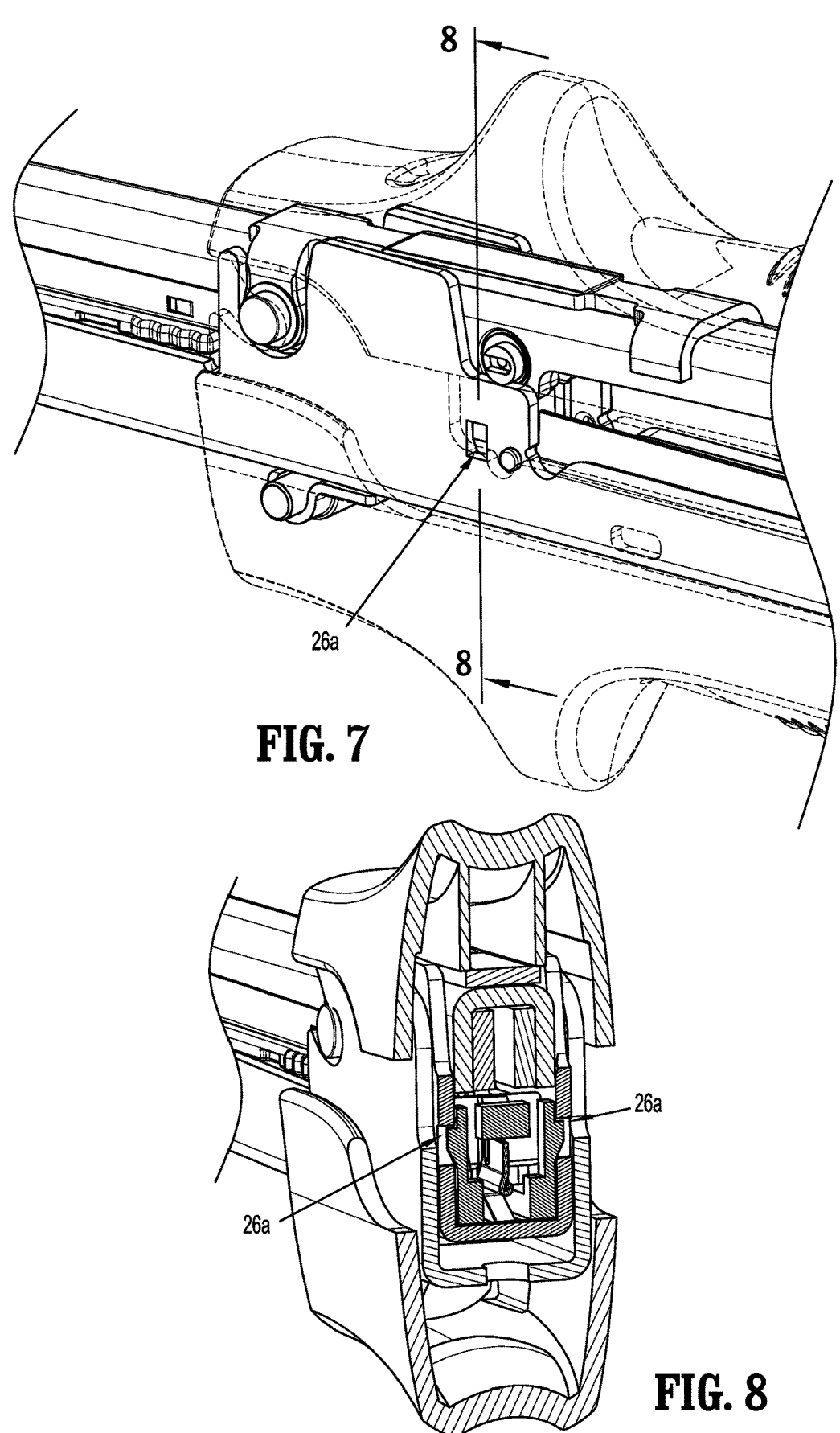
Figure 9:
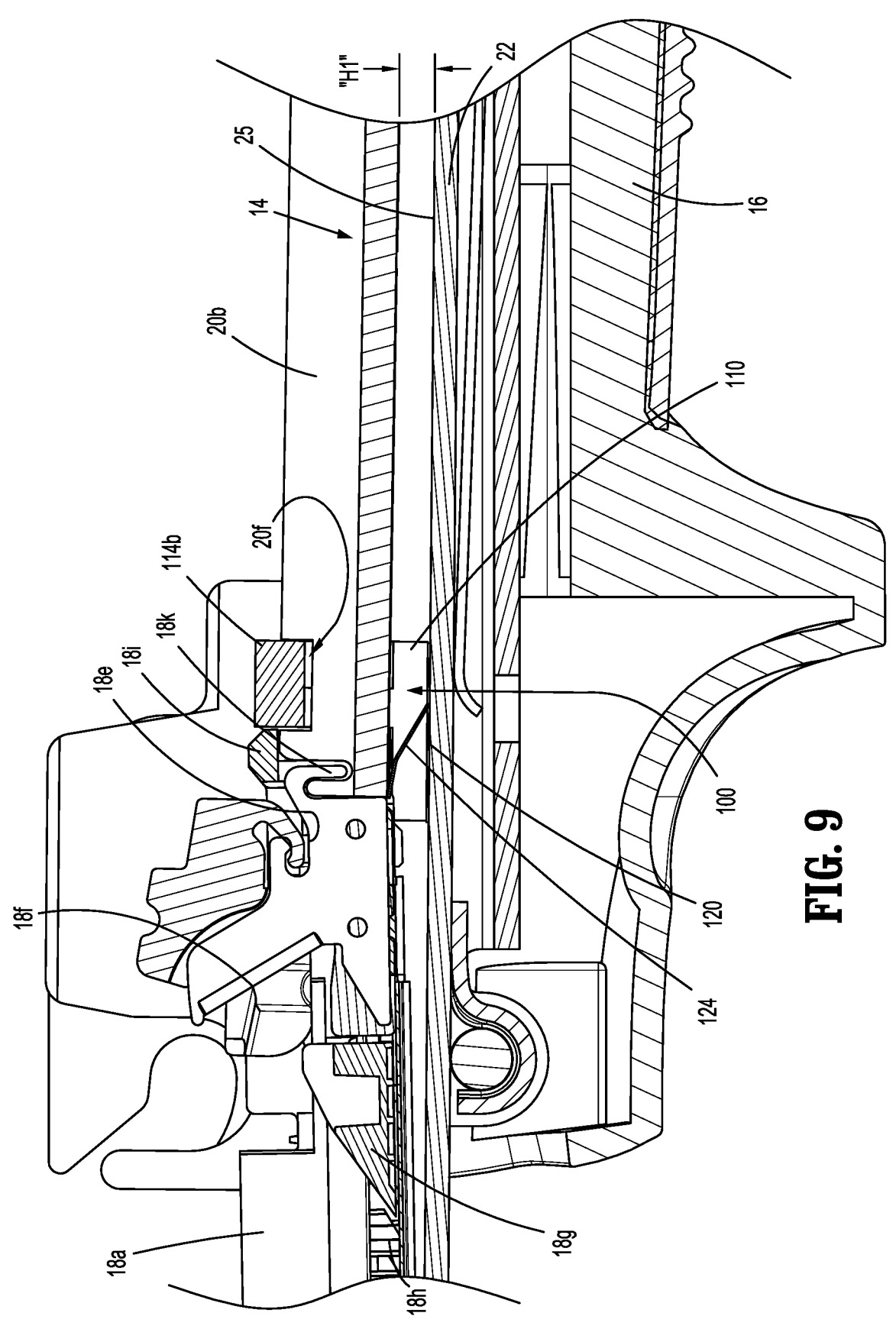
Figure 10:
Figure 11:
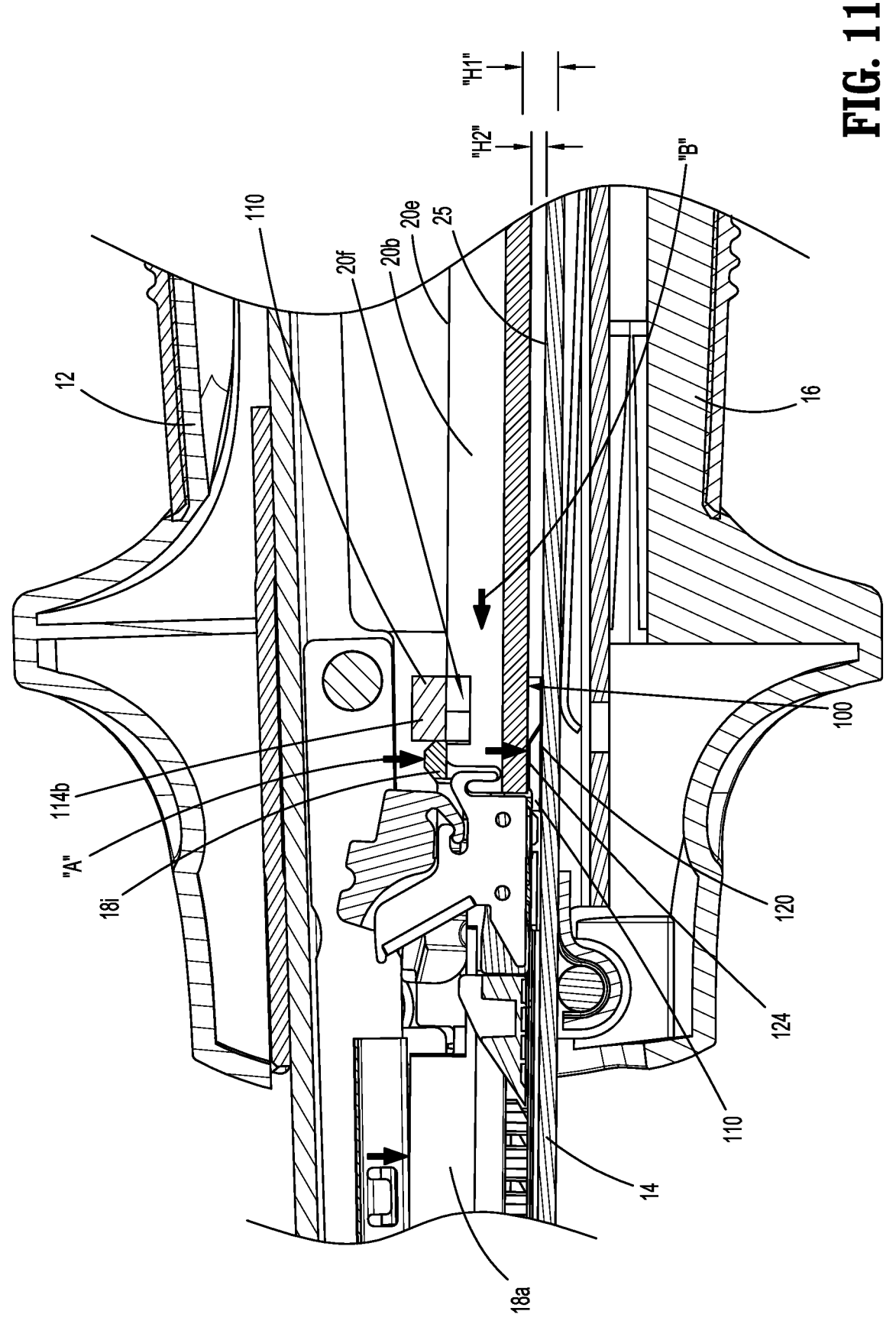

FIG. 1 is a perspective view, with parts separated, of a surgical stapling apparatus in accordance with the principles of this disclosure;

FIG. 2 is a perspective view, with parts separated, of portions of the surgical stapling apparatus of FIG. 1;

FIG. 3 is an enlarged, perspective view of the indicated area of detail shown in FIG. 2;

FIG. 4 is a perspective view, with parts separated, of FIG. 3;

FIG. 5 is a perspective view of a lockout of the surgical stapling apparatus of FIG. 1;

FIG. 6 is an enlarged, perspective view of a proximal portion of a cartridge assembly of the surgical stapling apparatus of FIG. 1;

FIG. 7 is an enlarged, perspective view of a central portion of the surgical stapling apparatus of FIG. 1, the surgical stapling apparatus illustrated in a locked position with portion in phantom for clarity;

FIG. 8 is a perspective, cross-sectional view of FIG. 7 as taken along section line 8-8 of FIG. 7;

FIG. 9 is an enlarged, cross-sectional view of the surgical stapling apparatus of FIGS. 1 and 2 as taken along section line 9-9 of FIG. 1;

FIG. 10 is a perspective view of the surgical stapling apparatus of FIG. 1, the surgical stapling apparatus illustrated in a clamped and unlocked position; and FIG. 11 is an enlarged, cross-sectional view of a central portion of FIG. 10 as taken along section line 11-11 of FIG. 10.

DETAILED DESCRIPTION

Aspects of this disclosure are described in detail with reference to the drawings, in which like reference numerals designate identical or corresponding elements in each of the several views. Additionally, the term "proximal" or "trailing" refers to the portion of structure that is closer to the clinician and the term "distal" or "leading" refers to the portion of structure that is farther from the clinician. As commonly known, the term "clinician" refers to a doctor (e.g., a surgeon), a nurse, or any other care provider and may include support personnel.

In the following description, well-known functions or constructions are not described in detail to avoid obscuring this disclosure in unnecessary detail.

Referring to FIGS. 1-11, and as best seen in FIGS. 1-4, surgical stapler or surgical stapling apparatus 10 defines a longitudinal axis "L" (see FIG. 10) and includes an anvil half-section 12 having an anvil 12a, a cartridge receiving half-section 14, a clamping lever 16, a cartridge assembly or single use loading unit 18 (hereinafter "SULU"), a firing assembly 20, and a lockout assembly 100 having a lockout 110 and spring unit 120 secured to lockout 110. As best seen in FIGS. 6 and 9, SULU 18 includes a cartridge body 18a having a tissue-contacting surface 18b that defines a plurality of rows of staple retention slots 18c therein and a longitudinal knife slot 18d therealong that separates the plurality of rows of staple retention slots 18c. Cartridge body 18a supports a drive beam 18e having a distal knife 18f supported thereon and a proximal finger 18k extending therefrom. Cartridge body 18a further supports a sled 18g that engages staple pushers 18h for firing staples of SULU 18 through the plurality of rows of staple retention slots 18c for forming against a corresponding plurality of rows of staple pockets (not shown) defined in anvil 12a. Cartridge body 18a further includes a proximal flange 18i that extends proximally therefrom.

Lockout assembly 100 prevents surgical stapler 10 from firing when anvil half-section 12 and cartridge receiving half-section 14 are not clamped together. In aspects, anvil half-section 12, cartridge receiving half-section 14 and clamping lever 16 are constructed to be reusable components and, as such, are constructed from a biocompatible material suitable for sterilization and repeated use, e.g., stainless steel. In contrast, SULU 18 and/or firing assembly 20 may be constructed to be disposable and, as such, may be constructed from any suitable biocompatible material, e.g., plastics, metals, combinations thereof, having the requisite strength characteristics. For a more detailed description of similar surgical staplers, one or more components of which can be included in surgical stapler 10, or modified for use with surgical stapler 10, reference can be made to U.S. Pat. Nos. 10,512,461 and 7,631,794, the entire contents of each of which are incorporated herein by reference.

With reference to FIGS. 2-4, firing assembly 20 of surgical stapler 10 includes a firing lever assembly 20a having a push plate 20b that extends distally from firing lever assembly 20a. Push plate 20b of firing assembly 20 extends distally to a distal finger 20c and defines a finger recess 20d proximal to distal finger 20c. Finger recess 20d of push plate 20b is positioned to receive proximal finger 18k of drive beam 18e to enable a the proximal end of drive beam 18e to interlock with the distal end of push plate 20b. Push plate 20b further includes an elongated ridge 20e along a top surface thereof. Elongated ridge 20e defines a lockout recess 20f therein. Cartridge receiving half-section 14 defines an elongated channel member 22 which defines a U-shaped channel 24 having a distal portion 24a configured to releasably receive SULU 18 and a proximal portion 24b configured to releasably receive firing assembly 20 therein. In general, when SULU 18 is supported in cartridge receiving half-section 14, anvil 12a and SULU 18 can be clamped together about tissue so that firing assembly 20 can be actuated to fire staples from SULU 18 and formed against anvil 12a for securing the staples to the clamped tissue. Elongated channel member 22 has base 25 and upright walls 26 that extend from base 25 on opposite sides thereof to support lockout assembly 100 in elongated channel member 22. As seen in FIGS. 7 and 8, upright walls 26 of elongated channel member 22 define support apertures 26a therethrough that enable lockout 110 to fixedly connect to upright walls 26 to prevent lockout 110 from moving relative to anvil half-section 12 or cartridge receiving half-section 14.

Referring to FIGS. 3-5, lockout 110 of lockout assembly 100 includes legs 112 that support a stop assembly 114 therebetween. Legs 112 of lockout 110 include feet 116 that extend distally from legs 112. Feet 116 include mounting nubs 116a that extend laterally from feet 116 to support spring unit 120 on lockout 110. Legs 112 further include shoulders 118 that extend laterally therefrom and are receivable within support apertures 26a of elongated channel member 22 to fixedly secure lockout assembly 100 to elongated channel member 22. Stop assembly 114 includes a support wall 114a and a stopper 114b supported on support wall 114a. Support wall 114a of stop assembly 114 defines a push plate passage 114c therethrough that enables push plate 20b of firing assembly 20 to advance through lockout 110. Stopper 114b of stop assembly 114 is receivable within lockout recess 20f of push plate 20b to prevent push plate 20b from freely advancing through push plate passage 114c of lockout 110.

Spring unit 120 of lockout assembly 100 includes a base 122 having a leaf spring 124 and side walls 126 that extend upwardly from base 122. Leaf spring 124 is disposed between side walls 126 and arranged at an acute angle relative to base 122. Leaf spring 124 is positioned to support a bottom surface of push plate 20b of firing assembly 20. Leaf spring 124 is flexibly movable between an unflexed position (FIG. 9) and a flexed position (FIG. 11) to enable firing assembly 20 to move between locked and unlocked positions. Side walls 126 of spring unit 120 define nub recess 126a therethrough that are positioned to receive mounting nubs 116a of lockout 110 therein to secure spring unit 120 to a bottom surface of lockout 110.

With reference to FIGS. 9-11, before anvil half-section 12 is secured to cartridge receiving half-section 14, SULU 18 is coupled to push plate 20b of firing assembly 20 and in a locked position such that the proximal end of SULU 18 and the distal end of push plate 20b are raised above base 25 of elongated channel member 22 at a first height "H1" so that push plate 20b and SULU 18 are slightly angled relative to elongated channel member 22 (e.g., so that push plate 20b and SULU 18 are sloping in opposite directions relative to on another). In this sloped and locked position, stopper 114b of lockout 110 is disposed in lockout recess 20f of push plate 20b to prevent push plate 20b from freely advancing past lockout assembly 100 (see FIG. 9) and thereby preventing drive beam 18e and sled 18g of SULU 18 from distally advancing through cartridge body 18a of SULU 18 and firing surgical stapling apparatus 10.

When anvil half-section 12 is secured to cartridge receiving half-section 14 to clamp anvil 12a and SULU 18 together, proximal flange 18i of SULU 18 drives downwardly against elongated ridge 20e of push plate 20b, as indicated by arrows "A," so that the bottom surface of push plate 20b engages leaf spring 124 of spring unit 120 causing leaf spring 124 to flex downwardly from the unflexed position to the flexed position. As leaf spring 124 flexes downwardly, the distal end of push plate 20b and the proximal end of SULU 18 approximate the base 25 of elongated channel member 22 to move push plate 20b vertically downward relative to stopper 114b of lockout 110 to separate stopper 114b from lockout recess 20f of push plate 20b. Such downward movement causes the distal end of push plate 20b and the proximal end of SULU 18 to move from the first height "H1" to a second height "H2" that is smaller than the first height "H1." At the first height "H1," surgical stapling apparatus 10 is disposed in a locked position, and at the second height "H2," the surgical stapling apparatus 10 is disposed in an unlocked position such that firing assembly 20 can be advanced distally through lockout assembly 100 for firing surgical stapling apparatus 10. At the second height "H2," the push plate 20b and SULU 18 are substantially parallel to base 25 of elongated channel member 22. In particular, with stopper 114b of lockout 110 separated from lockout recess 20f of pusher plate 20b of firing assembly 20, pusher plate 20b can be freely advanced through pusher plate passage 114c of lockout 110, as indicated by arrow "B," for distally advancing drive beam 18e and sled 18g of SULU 18 to fire surgical stapling apparatus 10 and to fasten and cut tissue clamped between SULU 18 and anvil 12a of surgical stapling apparatus 10.

Persons skilled in the art will understand that the structures and methods specifically described herein and illustrated in the accompanying figures are non-limiting exemplary embodiments, and that the description, disclosure, and figures should be construed merely as exemplary of particular aspects. It is to be understood, therefore, that this disclosure is not limited to the precise aspects described, and that various other changes and modifications may be effected by one skilled in the art without departing from the scope or spirit of this disclosure. Additionally, it is envisioned that the elements and features illustrated or described in connection with one exemplary aspect may be combined with the elements and features of another without departing from the scope of this disclosure, and that such modifications and variations are also intended to be included within the scope of this disclosure. Indeed, any combination of any of the disclosed elements and features is within the scope of this disclosure. Accordingly, the subject matter of this disclosure is not to be limited by what has been particularly shown and described.

What is claimed is:

1. A surgical stapling apparatus comprising:
an anvil half-section;
a cartridge receiving half-section defining an elongated channel member, the elongated channel member configured to receive a single use loading unit (SULU);
a firing assembly including a push plate, the push plate having a distal end portion configured to selectively interlock with a proximal end portion of a drive beam; and
a lockout assembly supported in the elongated channel member and including a spring unit and a lockout that is selectively engageable with the push plate to prevent movement of the push plate relative to the lockout assembly when the anvil half-section and the cartridge receiving half-section are not secured together, wherein a proximal flange of the SULU is configured to drive the push plate downward, wherein the lockout comprises:
a first leg and a second leg;
a stop assembly supported between the first and second leg;
a first foot extending distally from the first leg;
a second foot extending distally from the second leg;
a first mounting nub extending laterally outward from the first foot; and
a second mounting nub extending laterally outward from the second foot, wherein the spring unit is supported by the first mounting nub and the second mounting nub.

2. The surgical stapling apparatus of claim 1, wherein the stop assembly includes a stopper and wherein the push plate defines a lockout recess that is configured to receive the stopper.

3. The surgical stapling apparatus of claim 1, wherein the spring unit is positioned in engagement with the push plate.

4. The surgical stapling apparatus of claim 3, wherein the spring unit includes a leaf spring that contacts the push plate and biases the push plate in a locked position.

5. The surgical stapling apparatus of claim 4, wherein the leaf spring is positioned to move between a first position and a second position, wherein in the first position, the lockout maintains the push plate in the locked position and prevents the push plate from moving distally beyond the lockout, and wherein in the second position, the push plate is positioned to advance through the lockout.

6. The surgical stapling apparatus of claim 5, wherein the lockout defines a push plate passage through a support wall of the lockout.

7. The surgical stapling apparatus of claim 6, wherein the support wall of the lockout is supported between the first and second legs of the lockout.

8. The surgical stapling apparatus of claim 7, wherein the legs include shoulders that are receivable by support apertures defined in the elongated channel member to fixedly secure the lockout to the elongated channel member.

9. The surgical stapling apparatus of claim 5, the proximal flange vertically movable relative to the elongated channel member to move the leaf spring from the first position to the second position.

10. The surgical stapling apparatus of claim 1, wherein the spring unit defines:

a first recess that receives the first mounting nub; and a second recess that receives the second mounting nub.

11. The surgical stapling apparatus of claim 10, wherein the spring unit comprises:

a base secured to a bottom surface of the lockout;

a first sidewall that extends laterally outside the first foot and upwardly from the base, wherein the first recess is defined in the first sidewall; and a second sidewall that extends that extends laterally outside of the second foot and upwardly from the base, wherein the second recess is defined in the second sidewall.

12. A surgical stapling apparatus comprising:

an anvil half-section;

a cartridge receiving half-section defining an elongated channel member, the elongated channel member configured to receive a single use loading unit (SULU);

a push plate having a distal end portion configured to selectively interlock with a proximal end portion of a drive beam; and a lockout assembly including a lockout that is selectively engageable with the push plate to lock the push plate at an acute angle relative to the elongated channel member when the anvil half-section and the cartridge receiving half-section are not secured together, wherein a proximal flange of the SULU is configured to drive the push plate downward, wherein the lockout comprises legs having feet extending distally therefrom, wherein the feet include mounting nubs extending laterally outward therefrom to secure a spring unit to the lockout.

13. The surgical stapling apparatus of claim 12, wherein the lockout assembly includes a stopper and wherein the push plate defines a lockout recess that maintains the stopper therein when the push plate is disposed at the acute angle relative to the elongated channel member.

14. The surgical stapling apparatus of claim 12, wherein the spring unit is positioned in engagement with the push plate to maintain the push plate at the acute angle.

15. The surgical stapling apparatus of claim 14, wherein the spring unit includes a leaf spring that contacts the push plate.

16. The surgical stapling apparatus of claim 15, wherein the leaf spring is positioned to move between a first position and a second position, wherein in the first position, the lockout prevents the push plate from moving distally beyond the lockout, and wherein in the second position, the push plate is positioned to advance through the lockout.

17. The surgical stapling apparatus of claim 16, wherein the lockout defines a push plate passage through a support wall of the lockout to enable the push plate to advance through the lockout when the leaf spring is disposed in the second position.

18. The surgical stapling apparatus of claim 17, wherein the support wall of the lockout is supported between the legs of the lockout and extends above the leaf spring.

19. The surgical stapling apparatus of claim 18, wherein the legs include shoulders received in support apertures defined in the elongated channel member to prevent the lockout from moving relative to the elongated channel member.

20. The surgical stapling apparatus of claim 16, wherein the proximal flange is movable relative to the elongated channel member to move the leaf spring from the first position to the second position.

* * * * *